(12) United States Patent
Girod et al.

(10) Patent No.: US 10,639,121 B2
(45) Date of Patent: May 5, 2020

(54) SURGICAL INSTRUMENTATION SET

(71) Applicant: NOVASTEP, St. Gregoire (FR)

(72) Inventors: Loïc Girod, Goven (FR); Rémi Le Besque, Bruz (FR); Nicholas E Zelensky, Rosendale, NY (US)

(73) Assignee: NOVASTEP, St. Gregoire (FR)

(*) Notice: Subject to any disclaimer, the term of this patent is extended or adjusted under 35 U.S.C. 154(b) by 48 days.

(21) Appl. No.: 15/576,506

(22) PCT Filed: Jul. 11, 2016

(86) PCT No.: PCT/FR2016/051781
§ 371 (c)(1),
(2) Date: Nov. 22, 2017

(87) PCT Pub. No.: WO2017/009571
PCT Pub. Date: Jan. 19, 2017

(65) Prior Publication Data
US 2018/0168765 A1 Jun. 21, 2018

(30) Foreign Application Priority Data
Jul. 16, 2015 (FR) .................... 15 56718

(51) Int. Cl.
*A61B 50/30* (2016.01)
*A61C 3/04* (2006.01)
(Continued)

(52) U.S. Cl.
CPC .............. *A61B 50/30* (2016.02); *A61B 50/22* (2016.02); *A61B 50/312* (2016.02); *A61C 3/04* (2013.01);
(Continued)

(58) Field of Classification Search
CPC ....... A61B 50/22; A61B 50/312; A61B 50/30; A61B 2050/311; A61C 19/05; A61C 3/04;
(Continued)

(56) References Cited

U.S. PATENT DOCUMENTS 1,187,364 A * 6/1916 Monnot .................. A61C 3/04
                                                                206/210
1,525,858 A * 2/1925 Farrell, Jr. .............. A61F 17/00
                                                                206/227
(Continued)

FOREIGN PATENT DOCUMENTS

| FR | 912 281 A | 8/1946 |
| FR | 2 580 490 A1 | 10/1986 |
| GB | 2 396 550 A | 6/2004 |

OTHER PUBLICATIONS

Oct. 7, 2016 Written Opinion issued in International Patent Application No. PCT/FR2016/051781.
(Continued)

*Primary Examiner* — Chun Hoi Cheung
(74) *Attorney, Agent, or Firm* — Oliff PLC

(57) ABSTRACT

A surgical instrumentation assembly including: a storage tube having a service opening, a sealing member for closing off the service opening, a plurality of surgical instruments for temporary use, and a holder comprising a plurality of attachment elements configured to detachably attach the surgical instruments to the holder. The storage tube contains the holder and the sterile surgical instruments when the sealing member closes off the service opening.

9 Claims, 3 Drawing Sheets

(51) Int. Cl.
*A61C 19/02* (2006.01)
*A61B 50/22* (2016.01)
*A61B 50/31* (2016.01)
*A61B 17/00* (2006.01)
*A61M 5/00* (2006.01)
*A61F 17/00* (2006.01)

(52) U.S. Cl.
CPC .............. *A61C 19/02* (2013.01); *A61F 17/00* (2013.01); *A61B 2050/311* (2016.02); *A61M 5/002* (2013.01); *A61M 5/008* (2013.01)

(58) Field of Classification Search
CPC ........ A61C 19/02; A61F 17/00; A61M 5/002; A61M 5/008
USPC .................................. 206/234, 370, 363–383
See application file for complete search history.

(56) References Cited

U.S. PATENT DOCUMENTS

| | | | | |
|---|---|---|---|---|
| 2,399,040 | A * | 4/1946 | Karle | A61B 17/06128 206/227 |
| 2,409,465 | A * | 10/1946 | Armbruster | A61F 17/00 206/226 |
| 2,413,858 | A * | 1/1947 | Borgeat | A61M 5/002 206/210 |
| 2,826,297 | A * | 3/1958 | Hein, Jr. | A61B 17/32 206/572 |
| 3,058,579 | A | 10/1962 | Morin et al. | |
| 3,964,926 | A * | 6/1976 | Westphal | B08B 3/04 134/117 |
| 4,327,060 | A * | 4/1982 | Nisii | A61C 3/04 206/210 |
| 4,856,648 | A | 8/1989 | Krueger | |
| 5,071,346 | A * | 12/1991 | Domaas | A61C 3/04 206/369 |
| 5,167,193 | A * | 12/1992 | Withers | F23G 5/448 110/242 |
| 7,069,828 | B2 * | 7/2006 | Huang | B25G 1/063 81/177.4 |
| 9,815,614 | B2 * | 11/2017 | Griffin | D04B 3/00 |
| 2015/0335854 | A1 * | 11/2015 | Dvarsater | A61M 25/002 604/544 |

OTHER PUBLICATIONS

Oct. 7, 2016 Search Report issued in International Patent Application No. PCT/FR2016/051781.

* cited by examiner

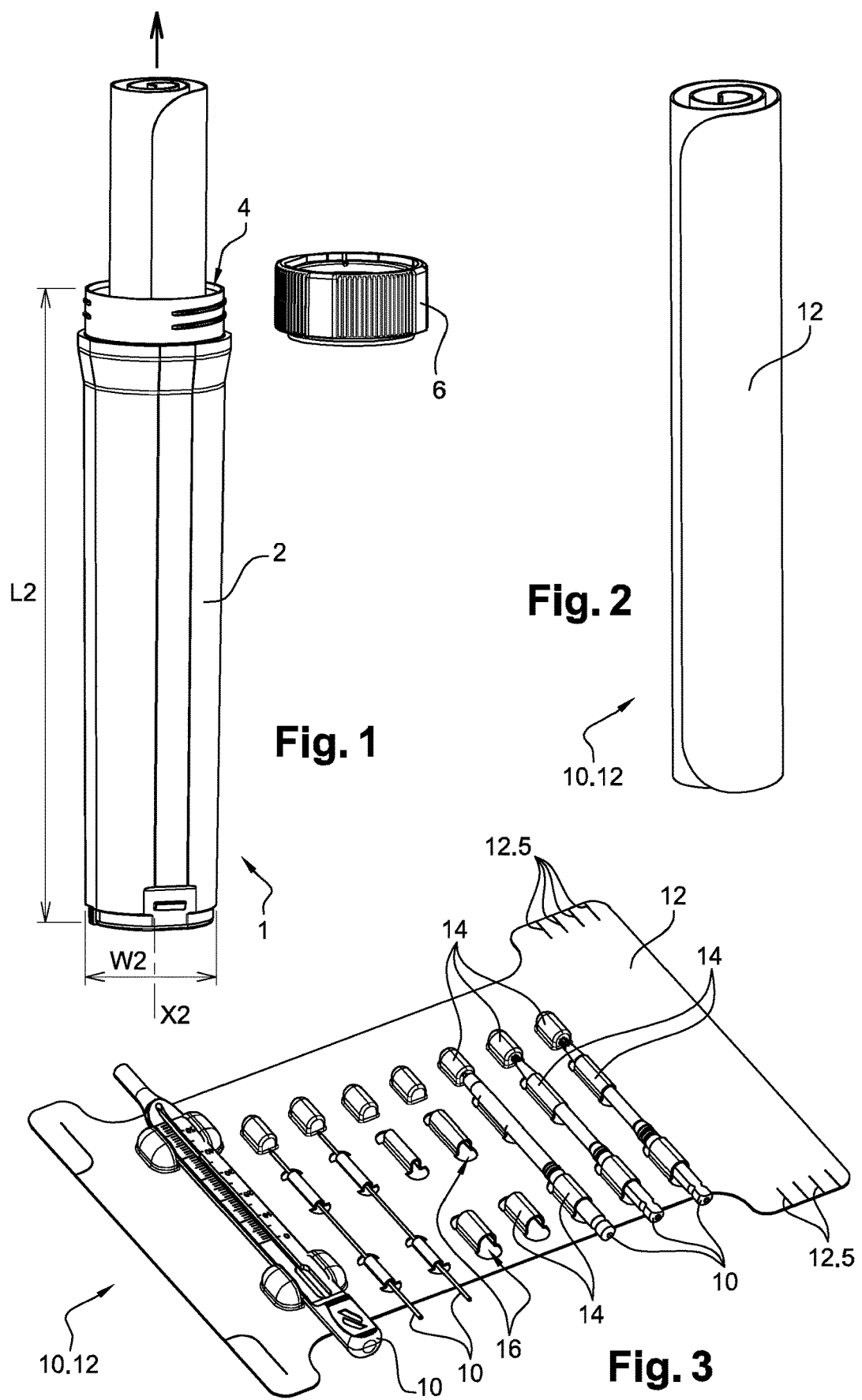

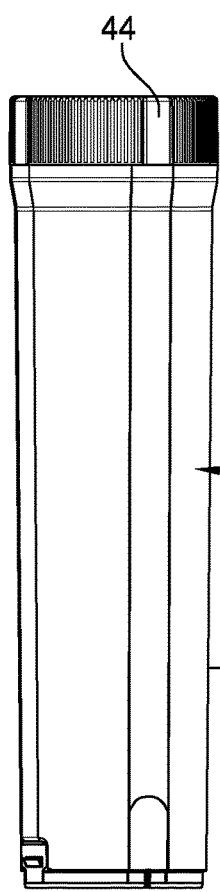 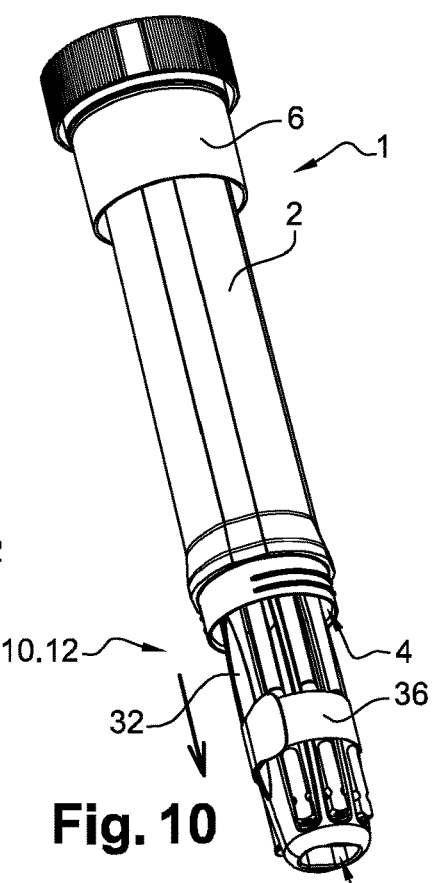 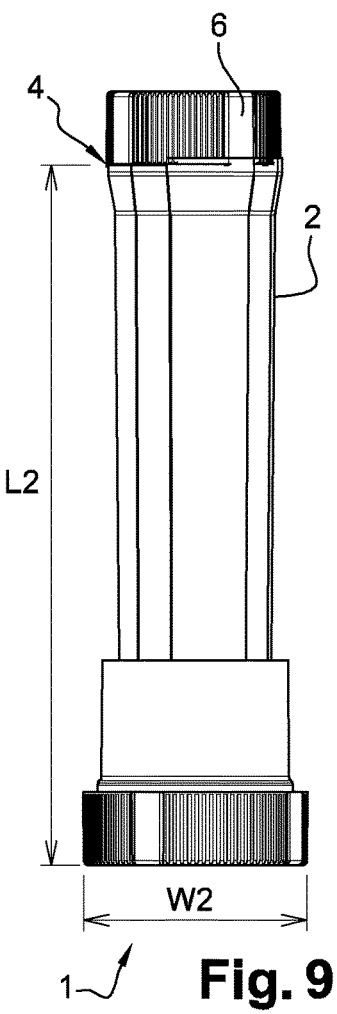
Fig. 8　Fig. 10　Fig. 9
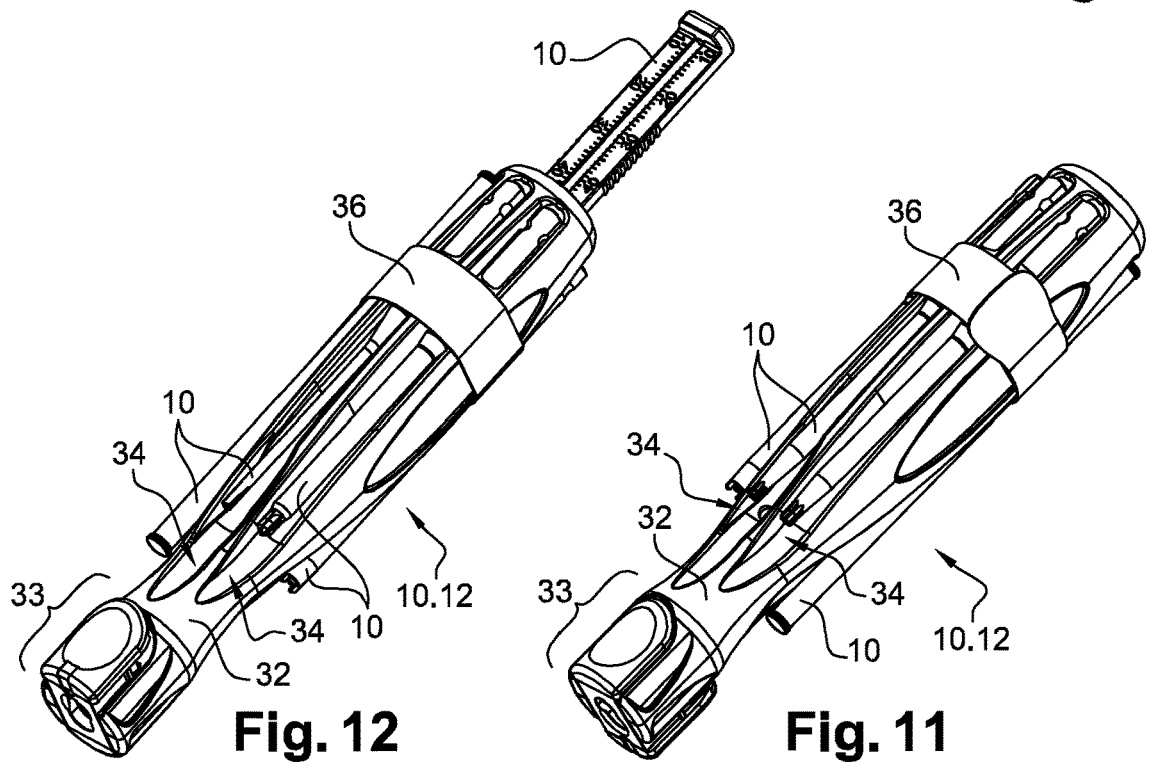
Fig. 12　Fig. 11

SURGICAL INSTRUMENTATION SET

The present invention concerns a surgical instrumentation set comprising several surgical instruments.

The present invention applies to the surgical field, for any surgical operation requiring setting surgical instruments at the disposal of the surgical team.

For example, the state of the art comprises a box in which numerous surgical instruments are packed, sometimes individually. Such a box has large dimensions, because it is versatile, in order to contain all the surgical instruments that might be necessary for several types of operations.

However, the surgical instrumentation sets of the state of the art are bulky. Furthermore, a surgical instrumentation set of the state of the art is relatively difficult to manipulate, which lengthens the duration of the surgical operation.

The aim of the present invention is in particular to solve, in whole or in part, the problems mentioned above. For this purpose, the object of the present invention is a surgical instrumentation set comprising at least:
- one storage tube having a service opening,
- one obturating member configured to obturate the service opening,
- several surgical instruments intended for a temporary use, and
- one support including several fastening elements configured to fasten the surgical instruments to the support in a detachable manner, the support and the surgical instruments forming a subset when the surgical instruments are fastened to the support;
- the storage tube being configured to house the subset, so as to store the subset in a sterile condition when the obturating member obturates the service opening, and the subset being shaped so as to be extracted from the storage tube through the service opening.

Thus, such a surgical instrumentation set allows storing several sterile surgical instruments in a compact manner, while enabling a rapid use in the operating room, because an operator can take out all the necessary surgical instruments in one single action.

In the present application, the term «storage tube» refers to an elongated hollow body, that is to say rather longer than broad. For example, this hollow body may have a generally cylindrical or prismatic shape.

In the present application, the term «surgical instrument» may refer to i) a complete surgical instrument, that a surgeon can manipulate in an autonomous manner, or ii) a portion of a surgical instrument, that a surgeon can assemble to another portion before manipulation.

According to one variant, the storage tube is configured to completely house the subset.

Alternatively to this variant, the storage tube is configured to house the major portion of the subset, and the obturating member is configured to house the rest of the subset. In this variant, a small portion of the subset projects out of the storage tube but it is covered by the obturating member. This variant allows forming a particularly compact surgical instrumentation set and it facilitates the gripping of the subset.

According to one embodiment, the surgical instruments are selected from the group consisting of screwdriver bits, drills, wires, tubular envelopes containing at least one wire, counterboring cutters, gauges and measuring rulers.

Thus, such surgical instruments allow performing most of the necessary gestures during an orthopedic surgical operation.

According to one variant, the number of surgical instruments is comprised between 2 and 15.

According to one embodiment, the service opening is located at one end of the storage tube.

Since the storage tube is a hollow body elongated according to a longitudinal direction, the storage tube has two opposite ends according to the longitudinal direction.

Alternatively to this embodiment, the service opening may be located on a lateral wall of the storage tube, this lateral wall extending between the opposite ends of the storage tube.

According to one variant, the obturating member is linked to the storage tube in a detachable manner.

Alternatively to this variant, the obturating member may be hinged to the storage tube so as to switch from an obturated position, in which the obturating member obturates the service opening, to an open position, in which the obturating member clears the service opening, the obturating member remaining linked to the storage tube. Thus, the obturating member cannot be lost in the operating room.

According to one embodiment, the support is at least partially flexible so as to switch:
- from a storage configuration, in which the support envelops the surgical instruments so that the subset may be housed in the storage tube,
- to a service configuration, in which the support is deployed so that an operator can detach the surgical instruments from the fastening elements.

Thus, such a support adds a protection to the surgical instruments in the storage configuration, while enabling the surgeon to easily access to all the surgical instruments in the service configuration.

In the present application, the term «flexible» describes a support sufficiently elastic to be folded up on itself in a reversible manner and without tearing, or sufficiently ductile to be bent, therefore plastically deformed, without breaking.

According to one variant, the support is completely flexible.

Alternatively, the support may have a flexible portion and a rigid portion.

According to one variant, the support is composed of a thermoplastic material. In particular, the support may be composed of a material selected from the group consisting of a polyethylene terephthalate glycol (PETG), a polycarbonate (PC) and a polypropylene.

According to one embodiment, the support is in the rolled-up state in the storage configuration and in the rolled-out state in the service configuration.

Alternatively to this embodiment, the support is in a folded state in the storage configuration and in an unfolded state in the service configuration. For example, the support may form several superimposed plies, for example in a fan-folded manner.

According to one embodiment, at least one portion of the fastening elements form passages, each passage being configured to pass at least one portion of a respective surgical instrument.

Thus, such passages allow fastening surgical instruments rapidly.

According to one embodiment, the support comprises a rod, the fastening elements being secured to the rod, the fastening elements being distributed over the circumference of the rod.

Thus, such a rod forms a barely bulky support enabling easy access to all the surgical instruments.

According to one variant, the fastening elements are distributed over the entire circumference of the rod.

According to one variant, the rod is substantially parallel to a longitudinal direction of the storage tube when the subset is housed in the storage tube.

According to one embodiment, the support has a basis disposed at an end region of the rod, the basis being configured to rest on a horizontal surface.

Thus, such a basis allows installing the subset in the operating room rapidly, for example by setting it on a table.

According to one embodiment, the rod has a gripping portion located in an end region of the rod, the gripping portion being located close to the service opening when the storage tube houses the subset.

Thus, such a gripping portion allows grabbing the subset in the storage tube rapidly, and then extracting the subset from the storage tube rapidly.

In the variant where the support comprises a basis, the gripping portion may be located in the end region opposite to the basis.

According to one embodiment, the fastening elements comprise at least one collar configured to fasten at least one of the surgical instruments by elastic snap-fit.

According to one variant, this collar is configured to fasten one of the surgical instruments by elastic snap-fit. Alternatively to this variant, this collar is configured to fasten one of the surgical instruments by a cylinder-on-cylinder frictional contact.

According to one variant, this collar has several holes for fastening several ones of the surgical instruments respectively. Each surgical instrument may be fitted in a respective hole.

According to one embodiment, the support comprises a handle adapted to be manipulated by an operator, the handle having an attachment portion configured to selectively attach one of the surgical instruments in a detachable manner.

Thus, such a handle allows defining a compact and autonomous surgical instrumentation set, because the handle allows the surgeon to manipulate the surgical instruments.

According to one variant, the locking portion is configured for locking a surgical instrument.

According to one embodiment, fastening elements are formed by longitudinal grooves formed at the outer surface of the handle, each longitudinal groove being adapted to house a portion of a respective surgical instrument so as to fasten said surgical instrument by elastic snap-fit.

Thus, such longitudinal grooves allow forming a compact handle with the surgical instruments.

According to one variant, the fastening elements further comprise a ribbon arranged around the handle so as to retain surgical instruments.

According to one variant, the fastening elements further comprise a heat-shrinkable clamping element.

According to one embodiment, the handle has a central cavity adapted to house at least one surgical instrument.

Thus, this central cavity makes the instrumentation set particularly compact.

According to one embodiment, the storage tube has at least one translucent portion, for example a transparent portion.

Thus, such a storage tube allows checking the presence of all the surgical instruments necessary to a surgical operation, before opening the sterilized storage tube. According to one variant, the storage tube is completely translucent, for example completely transparent.

According to one embodiment, the storage tube (2) is composed of a material selected from the group consisting of a polyethylene terephthalate glycol (PETG), a polycarbonate (PC) and a polypropylene.

Thus, such a material allows manufacturing a storage tube resistant to impacts and vibrations, as well as to the sterilization process, for example a gamma-ray irradiation.

According to one embodiment, the storage tube has a length comprised between 70 mm and 300 mm, and wherein the storage tube has a transverse dimension, measured in a plane perpendicular to the length, comprised between 20 mm and 100 mm.

For example, in the variant where the storage tube is cylindrical with a circular base, the storage tube may have a diameter comprised between 20 mm and 100 mm:

According to one variant, a ratio between:
i) in the numerator: the bulk of the subset,
ii) in the denominator: the inner volume of the storage tube,
is comprised between 0.05% and 95%.

Thus, such a storage tube is particularly compact.

According to one embodiment, the surgical instrumentation set according to the invention, further comprising:
a protective tube configured to house the storage tube, and
an outer plug configured to plug the protective tube when the protective tube houses the storage tube.

Thus, such a protective tube allows protecting the storage tube, and therefore protecting the surgical instruments against high-intensity impacts.

The embodiments and variants mentioned above can be taken separately or according to any technically possible combination.

The present invention will be well understood and its advantages will also appear in view of the following description, given only by way of non-limiting example and made with reference to the appended schematic figures, wherein identical reference signs correspond to structurally and/or functionally identical or similar elements. In the appended schematic figures:

FIG. 1 is a perspective view of a surgical instruments set according to a first embodiment of the invention, in the open state ready for a surgical operation;

FIG. 2 is a perspective view of a subset belonging to the surgical instruments set of FIG. 1, in the rolled-up state;

FIG. 3 is a perspective view of the subset of FIG. 2, in the rolled-out state;

FIG. 8 is a front view of a surgical instruments set according to a third embodiment of the invention, in the closed and sterile state;

FIG. 9 is a front view of the surgical instruments set of FIG. 8, in a half-open state;

FIG. 10 is a perspective view of the surgical instruments set of FIG. 8, in the open state;

FIG. 11 is a perspective view, in a first state, of a subset belonging to the surgical instruments set of FIG. 8, the subset including several surgical instruments; and FIG. 12 is a perspective view, in a second state, of the subset of FIG. 11, the subset including several surgical instruments.

Figure 4:
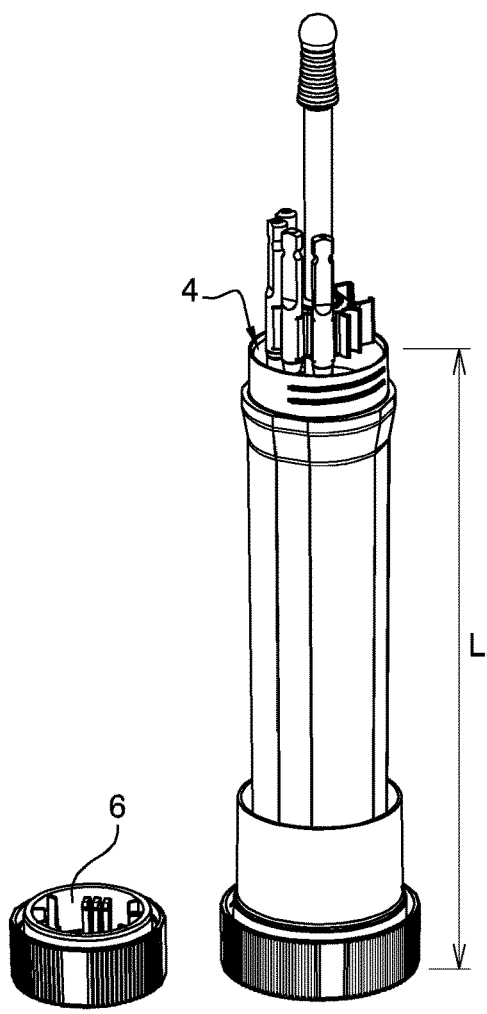
FIG. 4 is a perspective view of a surgical instruments set according to a second embodiment of the invention, in the closed and sterile state.

FIGS. 1, 2 and 3 illustrate a surgical instrumentation set 1 comprising a storage tube 2 having a service opening 4 and an obturating member 6 configured to obturate the service opening 4.

In addition, the surgical instrumentation set 1 comprises several surgical instruments 10 intended for a temporary use and a support 12 including several fastening elements 14. The fastening elements 14 are configured to fasten the surgical instruments 10 to the support 12 in a detachable manner. In the example of FIGS. 1 to 3, each fastening element 14 is configured to fasten a respective surgical instrument 10 to the support 12 in a detachable manner.

The support 12 and the surgical instruments 10 form a subset 10.12 when the surgical instruments 10 are fastened to the support 12, as illustrated in FIG. 3. Hence, the subset 10.12 comprises the support 12 and the surgical instruments 10. The surgical instruments 10 herein comprise screwdriver bits, drills, wires, a gauge and a measuring ruler.

The storage tube 2 is configured to completely house the subset 10.12, so as to store the subset 10.12 in a sterile condition when the obturating member 6 obturates the service opening 4. The storage tube 2 is a hollow body elongated according to a longitudinal direction X2. The storage tube 2 has two opposite ends according to the longitudinal direction X2.

The service opening 4 is herein located at one end of the storage tube 2. As illustrated in FIG. 1, the subset 10.12 is shaped so as to be extracted from the storage tube 2 through the service opening 4.

The support 12 is completely flexible so as to switch:
from a storage configuration (FIGS. 1 and 2), in which the support 12 envelops the surgical instruments 10 so that the subset 10.12 may be housed in the storage tube 2,
to a service configuration (FIG. 3), in which the support 12 is deployed so that an operator can detach the surgical instruments 10 from the fastening elements 14.

In the example of FIGS. 1 to 3, the support 12 is formed by a film composed of a plastic material. The support 12 is in the rolled-up state in the storage configuration (FIGS. 1 and 2) and in the rolled-out state in the service configuration (FIG. 3). The support 12 has pre-cut slots 12.5 which have the function of holding the film in the rolled-up state. To this end, each pre-cut slot may receive a portion of the film.

In the example of FIGS. 1 to 3, the fastening elements 14 form passages 16. Each passage 16 is configured to pass at least one portion of a respective surgical instrument 10. A passage 16 may be formed by cutting two parallel cut-outs on either side of a material bridge, so that this material bridge can retain a surgical instrument 10.

The surgical instrumentation set 1 allows storing several surgical instruments 10 in a compact manner and in a sterile condition, while enabling a rapid use in the operating room, because an operator can take out all the necessary surgical instruments 10 in one single action. In this instance, the support 12 allows retaining eight surgical instruments 10.

In order to fasten a surgical instrument 10 on the support 12, an operator can fit the surgical instrument 10 under the material bridge. In order to detach the surgical instrument 10 from the support 12, the operator has just to pull the surgical instrument 10 in order to slide it under the material bridge until releasing the surgical instrument 10, which is rapid.

Moreover, the storage tube 2 is completely transparent, which allows checking, before opening the storage tube 2, the presence of all the surgical instruments 10 necessary to a surgical operation. The storage tube 2 may be composed of polyethylene terephthalate glycol (PETG).

The storage tube 2 is herein cylindrical with a circular base having a diameter equal to about 30 mm. The storage tube 2 herein has a length L2 equal to about 150 mm and a transverse dimension W2 (diameter), measured in a plane perpendicular to the length L2, equal to about 30 mm.

FIGS. 4, 5, 6 and 7 illustrate a surgical instrumentation set 1 in accordance with a second embodiment. To the extent that the surgical instrumentation set 1 of FIGS. 4 to 7 is similar to the surgical instrumentation set 1 of FIGS. 1 to 3, the description of the surgical instrumentation set 1 given hereinbefore in connection with FIGS. 1 to 3 may be transposed to the surgical instrumentation set 1 of FIGS. 4 to 7, with the exception of the notable differences set out hereinafter.

Figure 5:
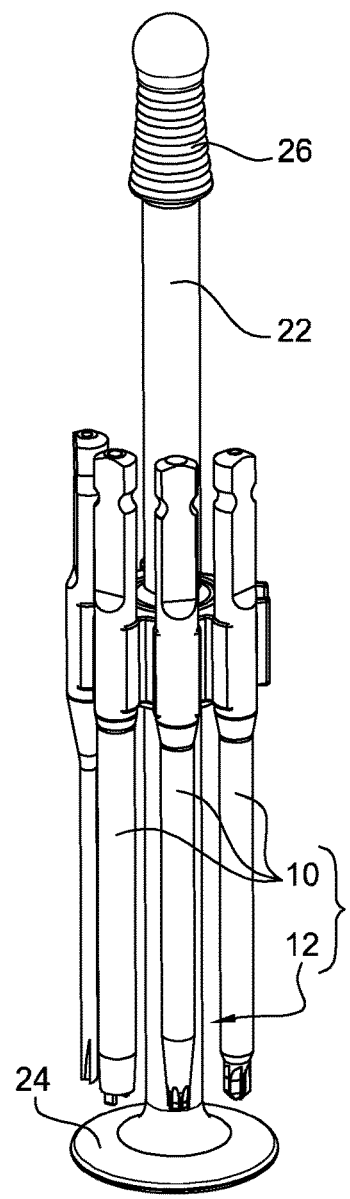
FIG. 5 is a perspective view of a subset belonging to the surgical instruments set of FIG. 4, the subset including several surgical instruments.
Figure 6:
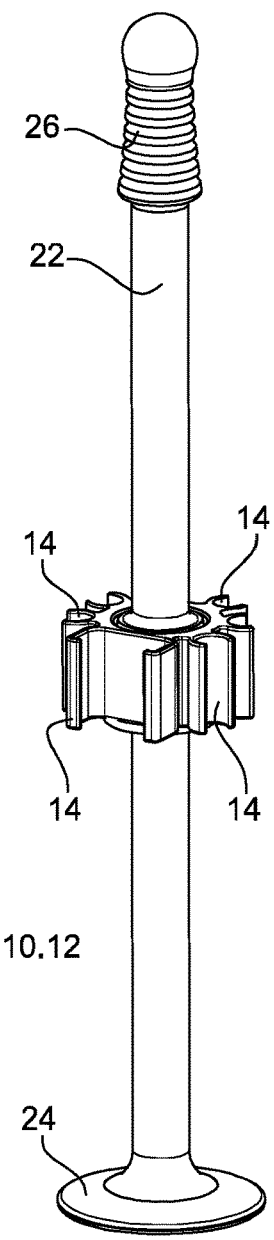
FIG. 6 is a perspective view of the subset of FIG. 5 devoid of the surgical instruments.
Figure 7:
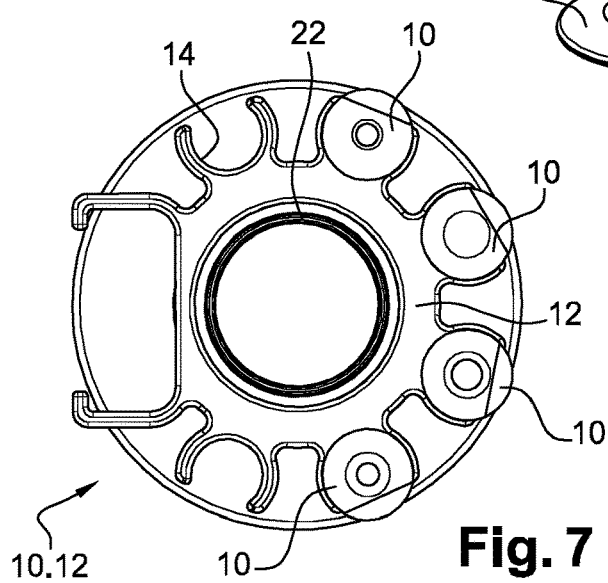
FIG. 7 is a top view of the subset of FIG. 5.

The surgical instrumentation set 1 of FIGS. 4 to 7 differs from the surgical instrumentation set 1 of FIGS. 1 to 3, in particular because the support 12 comprises a rod 22 to which the fastening elements 14 are secured, whereas the support 12 of FIGS. 1 to 3 is a flexible film. The fastening elements 14 are distributed over the circumference of the rod 22, as shown in FIG. 6.

The surgical instrumentation set 1 of FIGS. 4 to 7 differs from the surgical instrumentation set 1 of FIGS. 1 to 3, in particular because each fastening element 14 is herein formed by a collar which is elastically deformable so as to fasten surgical instruments 10 by elastic snap-fit. The fastening elements 14 are distributed over the entire circumference of the rod 22.

The rod 22 is substantially parallel to a longitudinal direction of the storage tube 2 when the subset 10.12 is housed in the storage tube 2, as illustrated in FIG. 5.

In this instance, the rod 22 and the fastening elements 14 allow retaining seven surgical instruments 10. An operator can pull a surgical instrument 10 away from the rod 22 in order to detach this surgical instrument 10. The rod 22 forms a barely bulky support 12 enabling easy access to all the surgical instruments 10.

Moreover, the rod 22 has a gripping portion 26 which is located in an end region of the rod 22. The gripping portion 26 is located close to the service opening 4 when the storage tube 2 houses the subset 10.12.

The gripping portion 26 allows an operator to grab the subset 10.12, and then extract it out of the storage tube 2. Afterwards, the gripping portion 26 allows holding the rod 22 in order to detach a surgical instrument 10 from the support 12.

The support 12 has a basis 24 disposed at an end region of the rod 22. In this instance, the basis 24 is located opposite to the gripping portion 26. The basis 24 is configured to rest on a horizontal surface in the operating room. The basis 24 is located in the end region opposite to the gripping portion 26.

Moreover, the surgical instrumentation set 1 of FIGS. 4 to 7 also comprises a non-represented protective tube, which is structurally and functionally similar to the protective tube 42 illustrated in FIG. 8.

FIGS. 8, 9, 10, 11 and 12 illustrate a surgical instrumentation set 1 in accordance with a second embodiment. To the extent that the surgical instrumentation set 1 of FIGS. 8 to 12 is similar to the surgical instrumentation set 1 of FIGS. 4 to 7, the description of the surgical instrumentation set 1 given hereinbefore in connection with FIGS. 4 to 7 may be transposed to the surgical instrumentation set 1 of FIGS. 8 to 12, with the exception of the notable differences set out hereinafter.

The surgical instrumentation set 1 of FIGS. 8 to 12 differs from the surgical instrumentation set 1 of FIGS. 4 to 7, in particular because the support 12 comprises a handle 32 adapted to be manipulated by an operator, whereas the surgical instrumentation set 1 of FIGS. 4 to 7 comprises the rod 22. The handle 32 has a locking portion 33 which is configured to selectively attach or detach (to the handle 32) one of the surgical instruments 10 in a detachable manner. The attachment portion 33 is configured to enable a rapid locking of a surgical instrument 10.

In addition, the surgical instrumentation set 1 of FIGS. 8 to 12 differs from the surgical instrumentation set 1 of FIGS. 4 to 7, in particular because most of the fastening elements 14 are formed by longitudinal grooves 34 formed at the outer surface of the handle 32, whereas the rod 22 includes collars for fastening the surgical instruments 10.

Each longitudinal groove 34 is adapted to house a portion of a respective surgical instrument 10 so as to fasten this surgical instrument 10 by elastic snap-fit. In this instance, the handle 32 allows retaining eight surgical instruments 10.

As illustrated in FIGS. 11 and 12, the fastening elements 14 further comprise a ribbon 36 which is arranged around the handle 32 so as to retain surgical instruments 10.

Furthermore, the surgical instrumentation set 1 of FIGS. 8 to 12 differs from the surgical instrumentation set 1 of FIGS. 4 to 7, in particular because the handle 32 has a central cavity 38 which is adapted to house at least one surgical instrument 10, in this instance a ruler, while the rod 22 is full.

The surgical instrumentation set 1 further comprises a protective tube 42 which is configured to house the storage tube 2. In addition, the surgical instrumentation set 1 comprises an outer plug 44 configured to plug the protective tube 42 when the protective tube 42 houses the storage tube 2.

The protective tube 42 and the outer plug 44 appear only in FIG. 8 illustrating the third embodiment. However, the first and second embodiments may also comprise a protective tube and an outer plug which are not represented.

Of course, the present invention is not limited to the particular embodiments described in the present patent application, nor to embodiments within the reach of those skilled in the art. Other embodiments can be considered without departing from the scope of the invention, from any element equivalent to an element indicated in the present patent application.

The invention claimed is:

1. A surgical instrumentation set comprising at least:
   one storage tube having a service opening,
   one obturating member configured to obturate the service opening,
   several surgical instruments intended for a temporary use, and
   one support including several fastening elements configured to fasten the surgical instruments to the support in a detachable manner, the support and the surgical instruments forming a subset when the surgical instruments are fastened to the support;
   the storage tube being configured to house the subset, so as to store the subset in a sterile condition when the obturating member obturates the service opening, and the subset being shaped so as to be extracted from the storage tube through the service opening;
   wherein the support comprises a handle adapted to be manipulated by an operator, said handle having a locking portion which is configured to selectively attach or detach one of the surgical instruments to the handle and having longitudinal grooves formed at the outer surface of the handle and extending from the locking portion to the opposite end of the handle wherein each longitudinal groove is adapted to house a portion of a respective surgical instrument so as to fasten this surgical instrument by elastic snap-fit, and further comprising a ribbon which is arranged around the handle.

2. The surgical instrumentation set according to claim 1, wherein the handle comprises a central cavity which is adapted to house at least one surgical element.

3. The surgical instrumentation set according to claim 1, wherein the surgical instruments are selected from the group consisting of screwdriver bits, drills, wires, tubular envelopes containing at least one wire, counterboring cutters, gauges, and measuring rulers.

4. The surgical instrumentation set according to claim 1, wherein the service opening is located at one end of the storage tube.

5. The surgical instrumentation set according to claim 1, wherein the storage tube has at least one translucent portion.

6. The surgical instrumentation set according to claim 5, wherein the at least one translucent portion is a transparent portion.

7. The surgical instrumentation set according to claim 1, wherein the storage tube is composed of a material selected from the group consisting of a polyethylene terephthalate glycol (PETG), a polycarbonate (PC), and a polypropylene.

8. The surgical instrumentation set according to claim 1, wherein the storage tube has a length between 70 mm and 300 mm, and wherein the storage tube has a transverse dimension, measured in a plane perpendicular to the length, between 20 mm and 100 mm.

9. The surgical instrumentation set according to claim 1, further comprising:
   a protective tube configured to house the storage tube, and
   an outer plug configured to plug the protective tube when the protective tube houses the storage tube.

* * * * *